United States Patent
Koh et al.

(10) Patent No.: US 7,460,909 B1
(45) Date of Patent: Dec. 2, 2008

(54) IMPLANTABLE DEVICE FOR MONITORING HEMODYNAMIC PROFILES

(75) Inventors: Steve Koh, South Pasadena, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 515 days.

(21) Appl. No.: 11/205,694

(22) Filed: Aug. 16, 2005

(51) Int. Cl.
*A61N 1/365* (2006.01)

(52) U.S. Cl. ......................................... 607/23; 600/526

(58) Field of Classification Search .................. 607/18, 607/19, 21–23; 600/483, 485, 502, 506, 600/513, 526
See application file for complete search history.

(56) References Cited

U.S. PATENT DOCUMENTS

| | | | | |
|---|---|---|---|---|
| 4,712,555 | A | 12/1987 | Thornander et al. | ... 128/419 PG |
| 4,788,980 | A | 12/1988 | Mann et al. | ........... 128/419 PG |
| 4,940,052 | A | 7/1990 | Mann et al. | ........... 128/419 PG |
| 5,156,147 | A * | 10/1992 | Warren et al. | .................. 607/24 |
| 5,466,254 | A | 11/1995 | Helland | ....................... 607/123 |
| 5,476,483 | A | 12/1995 | Bornzin et al. | ................. 607/17 |
| 5,782,883 | A * | 7/1998 | Kroll et al. | ..................... 607/14 |
| 6,314,323 | B1 | 11/2001 | Ekwall | ......................... 607/23 |
| 6,512,949 | B1 * | 1/2003 | Combs et al. | ................ 600/547 |
| 6,650,939 | B2 * | 11/2003 | Taepke et al. | .................. 607/27 |
| 6,682,481 | B2 * | 1/2004 | McKinley et al. | ........... 600/301 |
| 6,821,249 | B2 | 11/2004 | Casscells, III et al. | ...... 600/300 |
| 7,336,994 | B2 * | 2/2008 | Hettrick et al. | ................. 607/5 |
| 2003/0055345 | A1 | 3/2003 | Eigler et al. | ................. 600/486 |
| 2003/0055461 | A1 | 3/2003 | Girouard et al. | .............. 607/17 |
| 2003/0092975 | A1 | 5/2003 | Casscells, III et al. | ....... 600/300 |
| 2004/0147969 | A1 * | 7/2004 | Mann et al. | .................... 607/17 |

FOREIGN PATENT DOCUMENTS

| WO | WO 2004/026131 A1 | 1/2004 |
|---|---|---|
| WO | WO 2004/012815 A1 | 12/2004 |

OTHER PUBLICATIONS

Chaliki, Hari P MD et al., "*Pulmonary Venous Pressure: Relationship to Pulmonary Artery, Pulmonary Wedge, and Left Atrial Pressure in Normal, Lightly Sedated Dogs,*" Catheterization and Cardiovascular Interventions 56:432-438 (2002).

Deten, Alexander et al., "*Catheterization of Pulmonary Artery in Rats with Ultraminiature Catheter Pressure Transducer,*" Am J Physiol Heart Circ Physiol 285:H2213-H2217, 2003.

Drazner, Mark H. MD et al., "*Relationship between Right and Left-Sided Filling Pressures in 1000 Patients with Advanced Heart Failure,*" J Heart Lung Transplant 1999;18:1126-1132.

(Continued)

*Primary Examiner*—Kennedy J Schaetzle

(57) ABSTRACT

An exemplary method includes providing a filling pressure parameter, providing a perfusion parameter, determining a hemodynamic profile based at least in part on the filling pressure parameter and the perfusion parameter and adjusting a stimulation parameter of an implantable cardiac therapy device based at least in part on the hemodynamic profile. Other exemplary methods, devices, systems, etc., are also disclosed.

13 Claims, 12 Drawing Sheets

OTHER PUBLICATIONS

Grady, Kathleen L. PhD et al., "*Team Management of Patients with Heart Failure—A Statement for Healthcare Professionals from the Cardiovascular Nursing Council of the American Heart Association,*" Circulation. 2000;102-2443-2456.

Hofmann, Thomas MD et al., "*Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function,*" J Am Coll Cardiol 1995;26:23-49.

Rogers, John et al., Cardiovascular System Review, pp. 1-9 http://www.tc.umn.edu/~humbu001/resources/summary_layout_cv.pdf, Aug. 2005.

Shioi, Tetsuo MD, et al., "*Rapamycin Attenuates Lead-Induced Cardiac Hypertrophy in Mice,*" Circulation. 2003;107:1664-1670.

Tsukada, Kosuke et al., "*Development of Catheter-Type Optical Oxygen Sensor and Applications to Bioinstrumentation,*" Biosensors and Bioelectronics 18 (2003) 1439-1445.

Yamamoto, Kazuhiro MD et al., "*Assessment of Mean Left Atrial Pressure from the Left Ventricular Pressure Tracing in Patients with Cardiomyopathies,*" American Journal of Cardiology, vol. 78 (Jul. 1, 1996), pp. 107-110.

Zullo, Michael A. MD, "*Characteristics of the Acute Rise to Atrial Natriuretic Factor During Ventricular Pacing,*" Chest 2002;121:1942-1946.

* cited by examiner

Exemplary Parameters 300

FILLING PRESSURE 310

PERFUSION 320

Pressures 700

| Pressure | Possible Normal Value | Possible Limit Value |
|---|---|---|
| Pulmonary Wedge | ~ 4-12 mm Hg | ~ 20 mm Hg |
| Left Atrial | ~ 8-10 mm Hg | ~ 20 mm Hg |
| Pulmonary Artery - S | ~ 15-30 mm Hg | ~ 30 mm Hg |
| Pulmonary Artery - D | ~ 4-12 mm Hg | ~ 15 mm Hg |
| Mean Pulmonary Artery | ~ 10-12 mm Hg | ~ 15 mm Hg |
| Mean Right Atrial | ~ 2-6 mm Hg | ~ 10 mm Hg |
| LV Minimal | ~ 9 mm Hg | ~ 9 mm Hg |
| LV Pre-A | ~ 14 mm Hg | ~ 14 mm Hg |
| LVED | ~ 23 mm Hg | ~ 23 mm Hg |

Fig. 7

Perfusion Measures 800

IMPLANTABLE DEVICE FOR MONITORING HEMODYNAMIC PROFILES

TECHNICAL FIELD

Subject matter presented herein generally relates to monitoring hemodynamic profiles through use of an implantable device such as a cardiac therapy device. Various exemplary methods, devices, systems, etc., concern use of an implantable device to acquire information germane to a patient's hemodynamic profile.

BACKGROUND

An article by Grady et al., "Team Management of Patients With Heart Failure: A Statement for Healthcare Professionals from the Cardiovascular Nursing Council of the American Heart Association," *Circulation*, 2000; 102: 2443-2456, recognizes that significant effort has been devoted to development of an integrated approach to heart failure management. Indeed, a need exists for more effective measures for assessing heart failure. In particular, a need exists for robust means for hemodynamic profiling of patients and determining therapy in responsive thereto.

As described herein, various exemplary methods, devices, systems, etc., acquire information germane to a patient's hemodynamic profile and optionally respond to such information or communicate information to a care provider or appropriate external programmer to facilitate programming of an implantable therapy device.

SUMMARY

An exemplary method includes providing a filling pressure parameter, providing a perfusion parameter, determining a hemodynamic profile based at least in part on the filling pressure parameter and the perfusion parameter and adjusting a stimulation parameter of an implantable cardiac therapy device based at least in part on the hemodynamic profile. Other exemplary methods, devices, systems, etc., are also disclosed.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

FIG. 7 is a table of various pressures, possible normal values and possible limit values for use in determining a patient's hemodynamic profile.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices, systems, etc., described herein pertain to hemodynamic profiling of patients fitted with an implantable device. Various parameters are presented along with an exemplary scheme for profiling. An exemplary implantable device may acquire information via in vivo measurements or via communication with one or more other devices or sensors. Various exemplary methods, devices, systems, etc., optionally adjust patient therapy based at least in part on hemodynamic profile or trends in hemodynamic profile.

Exemplary Stimulation Device

The techniques described below are optionally implemented in connection with any stimulation device that is configured or configurable to stimulate and/or shock tissue.

Figure 1:
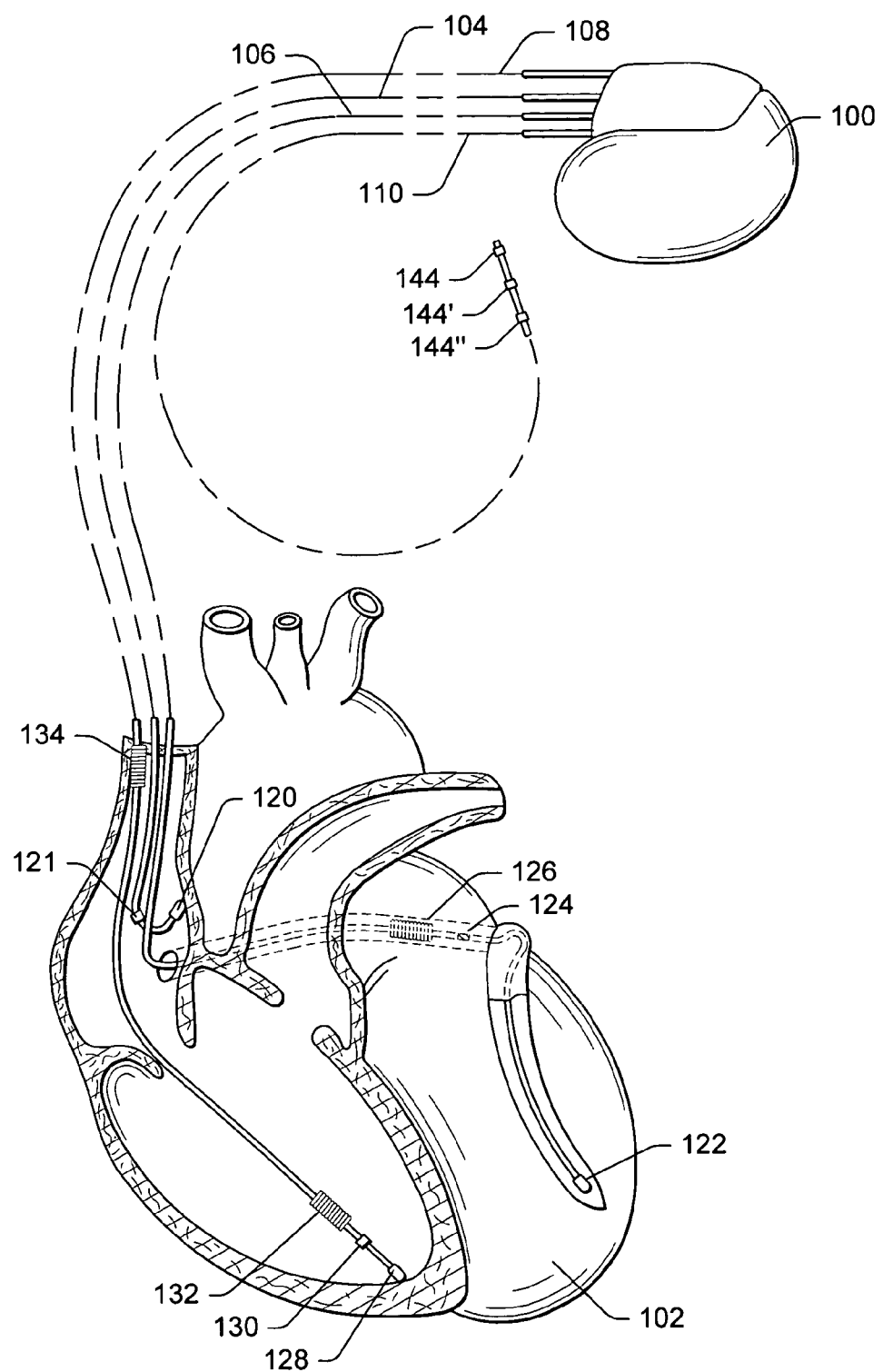
FIG. 1 is a simplified diagram illustrating an exemplary implantable stimulation device in electrical communication with at least three leads implanted into a patient's heart and at least one other lead for delivering stimulation and/or shock therapy. The exemplary stimulation device optionally includes one or more sensors for measuring information germane to a patient's hemodynamic profile.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
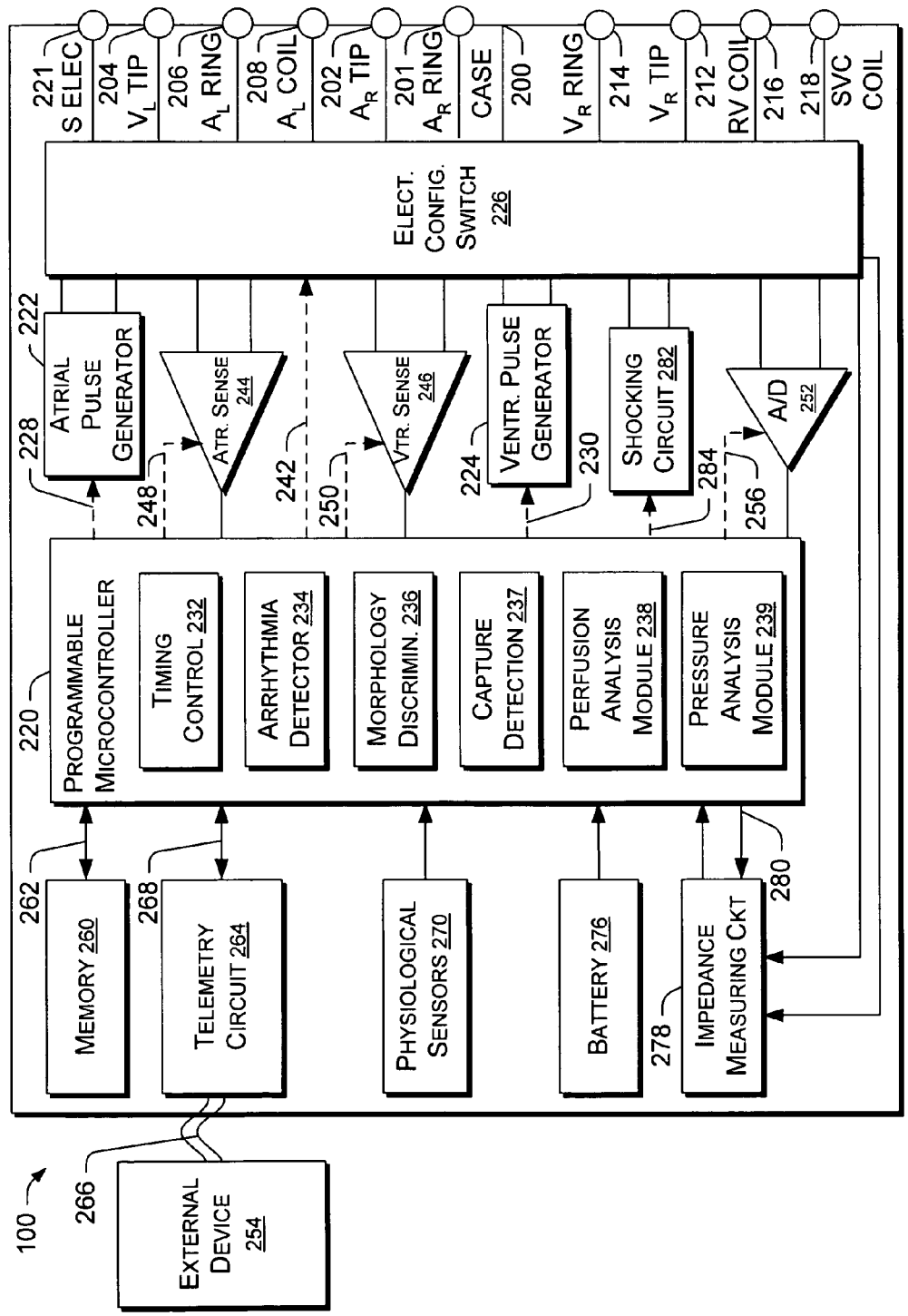
FIG. 2 is a functional block diagram of an exemplary implantable stimulation device illustrating basic elements that are configured to provide cardioversion, defibrillation, pacing stimulation or other tissue or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, a perfusion analysis module 238, a pressure analysis module 239 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The perfusion analysis module 238 may perform a variety of tasks related to one or more measures of perfusion and the pressure analysis module 239 may perform a variety of tasks related to one or measures of filling pressure. The perfusion analysis module 238 or the pressure analysis module 239 component are optionally utilized by the stimulation device 100 in determining a patient's hemodynamic profile.

The perfusion analysis module 238 and the pressure analysis module 239 may be implemented in hardware as part of the microcontroller 220, or as software/firmware instructions programmed into the device and executed on the microcontroller 220 during certain modes of operation. The perfusion analysis module 238 and the pressure analysis module 239 may optionally implement various exemplary methods described herein. The perfusion analysis module 238 and the pressure analysis module 239 may interact with the physiological sensors 270, the impedance measuring circuit 278 and optionally other modules.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

Pressure sensors for sensing left atrial pressure are discussed in U.S. Patent Application US2003/0055345 A1, to Eigler et al., which is incorporated by reference herein. The discussion pertains to a pressure transducer permanently implantable within the left atrium of the patient's heart and operable to generate electrical signals indicative of fluid pressures within the patient's left atrium. According to Eigler et al., the pressure transducer is connected to a flexible electrical lead, which is connected in turn to electrical circuitry, which includes digital circuitry for processing electrical signals. Noted positions of the transducer include within the left atrium, within a pulmonary vein, within the left atrial appendage and in the septal wall.

The exemplary device 100 optionally includes a connector capable of connecting a lead that includes a pressure sensor. For example, the connector 221 optionally connects to a pressure sensor capable of receiving information pertaining to chamber pressures or other pressures. Pressure information is optionally processed or analyzed by the pressure analysis module 239.

A study by Hofmann et al., "Simultaneous measurement of pulmonary venous flow by intravascular catheter Doppler velocimetry and transesophageal Doppler echocardiography: relation to left atrial pressure and left atrial and left ventricular function", *J Am Coll Cardiol*. 1995 July; 26(1):239-49, used a "microtip" pressure transducer and noted that mean left atrial pressure was strongly correlated with the ratio of systolic to diastolic peak velocity, systolic velocity-time integral, time to maximal flow velocity and the ratio of systolic to diastolic flow duration. In particular, Hofmann et al. reported that the ratio of systolic to diastolic peak velocity and the time to maximal flow velocity were identified as strong independent predictors of mean left atrial pressure and that left atrial compliance was not found to be an independent predictor of mean left atrial pressure. This study indicates that surrogates may exist for indirect measurement or estimation of left atrial pressure or mean left atrial pressure.

Commercially available pressure transducers include those marketed by Millar Instruments (Houston, Tex.) under the mark MIKROTIP®. A study by Shioi et al., "Rapamycin Attenuates Load-Induced Cardiac Hypertrophy in Mice", *Circulation* 2003; 107:1664, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., chamber of heart, vessel, etc.).

A study by Deten et al., "Catheterization of pulmonary artery in rats with an ultraminiature catheter pressure transducer," *Am J Physiol Heart Circ Physiol*, 285: H2212-H2217, 2003, reported use of an "ultraminiature" catheter pressure transducer for catheterization of the pulmonary artery. The transducer was obtained via Millar Instruments, model SPR-671 1.4 Fr catheter. Another company, Radi Medical Systems AB (Uppsala, Sweden), markets various lead-based sensors for intracoronary pressure measurements, coronary flow reserve measurements and intravascular temperature measurements. Such sensor technologies may be suitably adapted for use with an implantable device for in vivo measurements of physiology.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

The companies Nellcor (Pleasanton, Calif.) and Masimo Corporation (Irvine, Calif.) market pulse oximeters that may be used externally (e.g., finger, toe, etc.). Where desired, information from such external sensors may be communicated wirelessly to the implantable device, for example, via an implantable device programmer. Other sensors may be implantable and suitably connected to or in communication with the exemplary implantable device 100. Technology exists for lead-based oximeters. For example, a study by Tsukada et al., "Development of catheter-type optical oxygen sensor and applications to bioinstrumentation," *Biosens Bioelectron,* 2003 Oct. 15; 18(12):1439-45, reported use of a catheter-type optical oxygen sensor based on phosphorescence lifetime.

Perfusion related measures are discussed further below and may include pressure swing of systolic and diastolic blood pressure (narrow pulse pressure associated with hypoperfusion), cardiac output, contractility, and serum sodium level (e.g., decrease).

The exemplary device 100 optionally includes a connector capable of connecting a lead that includes a sensor for sensing information related to perfusion. For example, the connector 221 optionally connects to a sensor for sensing information related to perfusion. Such information is optionally processed or analyzed by the perfusion analysis module 238.

The physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

While an accelerometer may be included in the case of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Figure 3:
FIG. 3 is a diagram of two exemplary parameters that may be used individually or in combination to determine a patient's hemodynamic profile.
Figure 3:
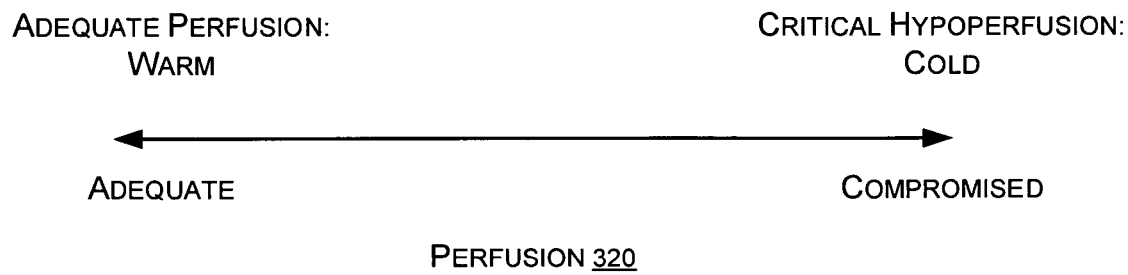

FIG. 3 shows exemplary parameters 300 germane to a patient's hemodynamic profile. A filling pressure parameter 310 ranges from normal or even below normal value to an elevated value. An elevated filling pressure is evidence of congestion whereas a normal filling pressure provides no evidence of congestion. As described by Grady et al., in the article "Team Management of Patients With Heart Failure: A Statement for Healthcare Professionals From the Cardiovascular Nursing Council of the American Heart Association," *Circulation*, 2000; 102:2443-2456, the resting hemodynamic profile of a patient can be defined in relationship to a filling pressure parameter where presence of evidence of an elevated filling pressure is associated with a "wet" profile and absence of evidence of an elevated filling pressure is associated with a "dry" profile.

A perfusion parameter 320 ranges from adequate perfusion or even more than adequate to compromised perfusion. As described by Grady et al., adequacy of tissue perfusion is associated with a "warm" profile while compromise of tissue perfusion is associated with a "cold" profile. As described herein, an exemplary device, method, system, etc., acquires evidence of filling pressure or adequacy of tissue perfusion to monitor a patient's hemodynamic profile. While filling pressure and tissue perfusion are given as exemplary parameters, other parameters may be used in various exemplary devices, methods, systems, etc.

Figure 4:
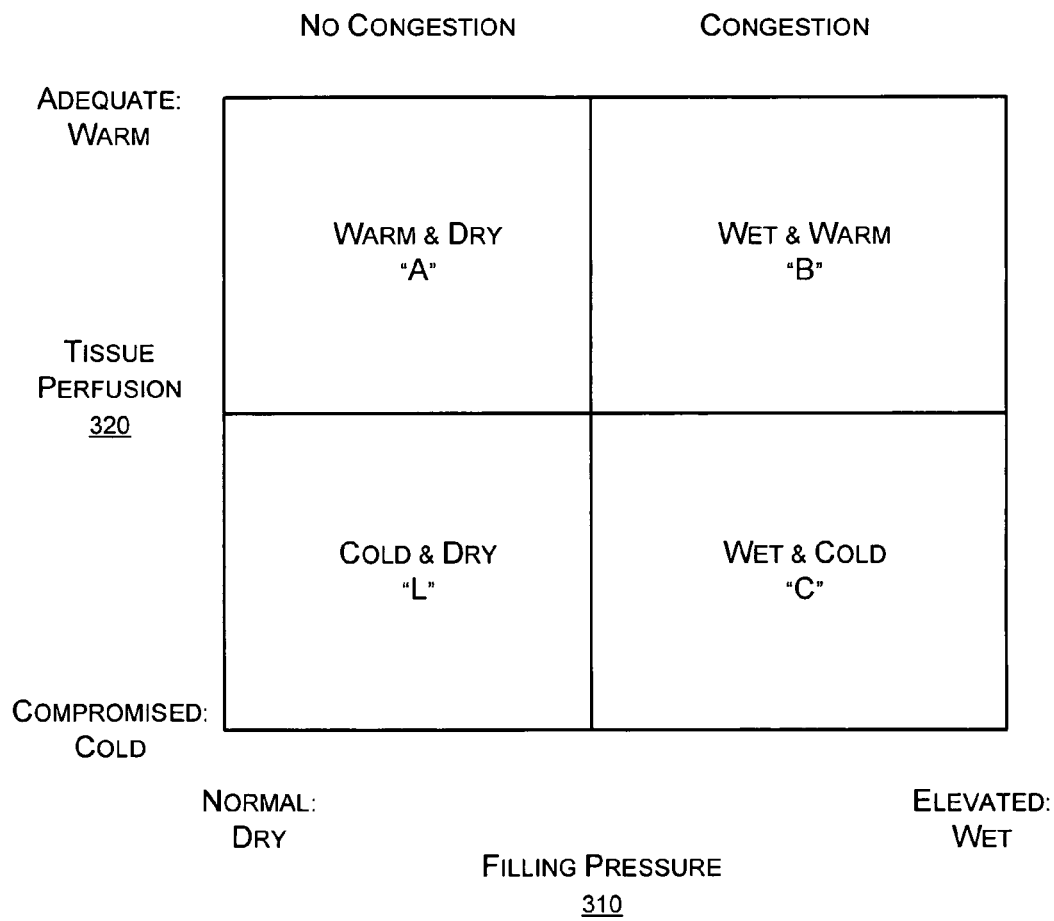
FIG. 4 is an exemplary scheme that relies on the two parameters of FIG. 3 to assess a patient's hemodynamic profile.

FIG. 4 shows a scheme 400 for assessing resting hemodynamic profile of a patient. The scheme 400 relies on the filling pressure parameter 310 and the perfusion parameter 320 and is described in the aforementioned article by Grady et al. The scheme 400 includes the profile terms "Warm & Dry", "Wet & Warm", "Wet & Cold" and "Cold & Dry", which are further associated with profile labels "A", "B", "C" and "L", respectively. According to Grady et al., the profile L represents a patient group with low output without congestion. Grady et al. further note that patients frequently progress from profile A to profile B and, when profile B occurs, profile C commonly follows.

Regarding patient treatment on the basis of profile, Grady et al. suggest that profile A is an optimal profile and that treatment should focus on prevention of disease progression and decompensation; for profile B, treatment may include diuresis with continuation of a standard therapy; for profile C, treatment may include diuresis and redesign of regimen with other standard therapies; and for profile L, limited options exist. In discussing the treatments, Grady et al. mention use of external defibrillation by family members of heart failure patients as one type of treatment; however, they state "data from these studies are controversial and do not yet support widespread training of family members" and that "further research is warranted".

As mentioned in the Background section, a need exists for hemodynamic profiling of patients and therapy responsive thereto, in turn, as described herein, an exemplary implantable device can acquire information germane to a patient's hemodynamic profile and optionally respond to such information or communicate the necessary information to a care provider or appropriate external programmer. Such exemplary devices, systems, methods, etc., generally allow a care provider to rely on existing diagnostic techniques when determining therapy of a patient fitted with an implantable cardiac therapy device.

Acquisition of information germane to a patient's hemodynamic profile may occur in any of a variety of manners. Acquisition may occur through in vivo measurement of physiological parameters, assessment of pacing or defibrillation parameters, communication with another device (implantable, external or hybrid of both), etc. Various measures of congestion and measures of perfusion, described below, serve as examples of acquisition of such information.

Figure 5:
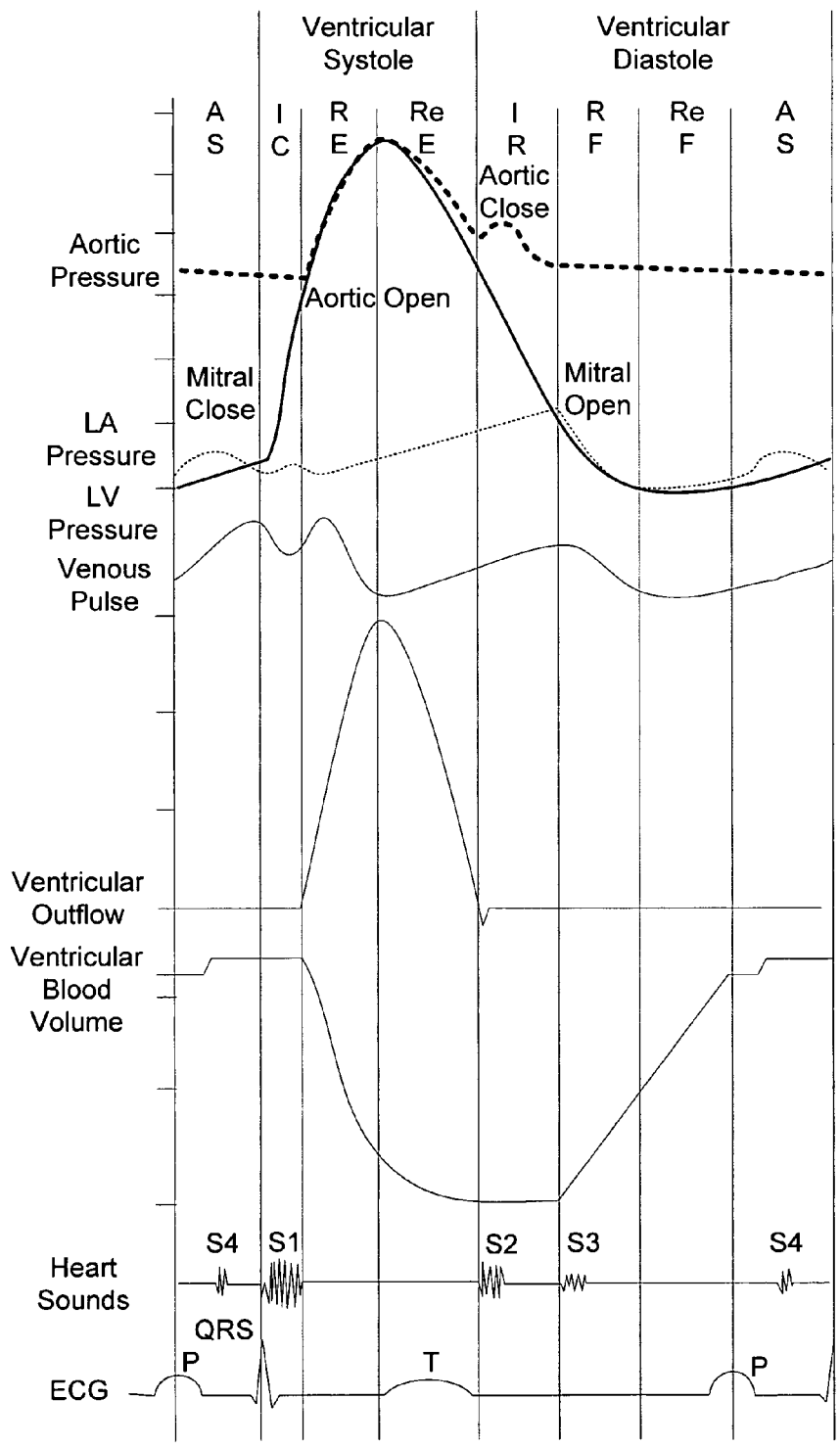
FIG. 5 is a diagram of various parameters and their variations during a cardiac cycle as typical of a Wigger diagram.

FIG. 5 shows a plot 500 of various parameters versus time during a cardiac cycle. The plot 500 is adapted from a Wigger diagram in an article entitled "Cardiovascular System Review" by Rogers and Humburg. The plot 300 shows various phases of the cardiac cycle including atrial systole (AS), isovolumic contraction (IS), rapid ejection (RE), reduced ejection (ReE), isovolumic relaxation (IR), rapid filling (RF), and reduced filling (ReF). In particular, the plot 500 illustrates how various parameters vary during ventricular systole and diastole. The parameters include aortic pressure, left atrial pressure, left ventricular pressure, venous pulse, ventricular outflow, ventricular volume, heart sounds, electrical activity (e.g., electrocardiogram) and valve dynamics. As described herein, any of a variety of parameters may be used for hemodynamic profiling.

Figure 6:
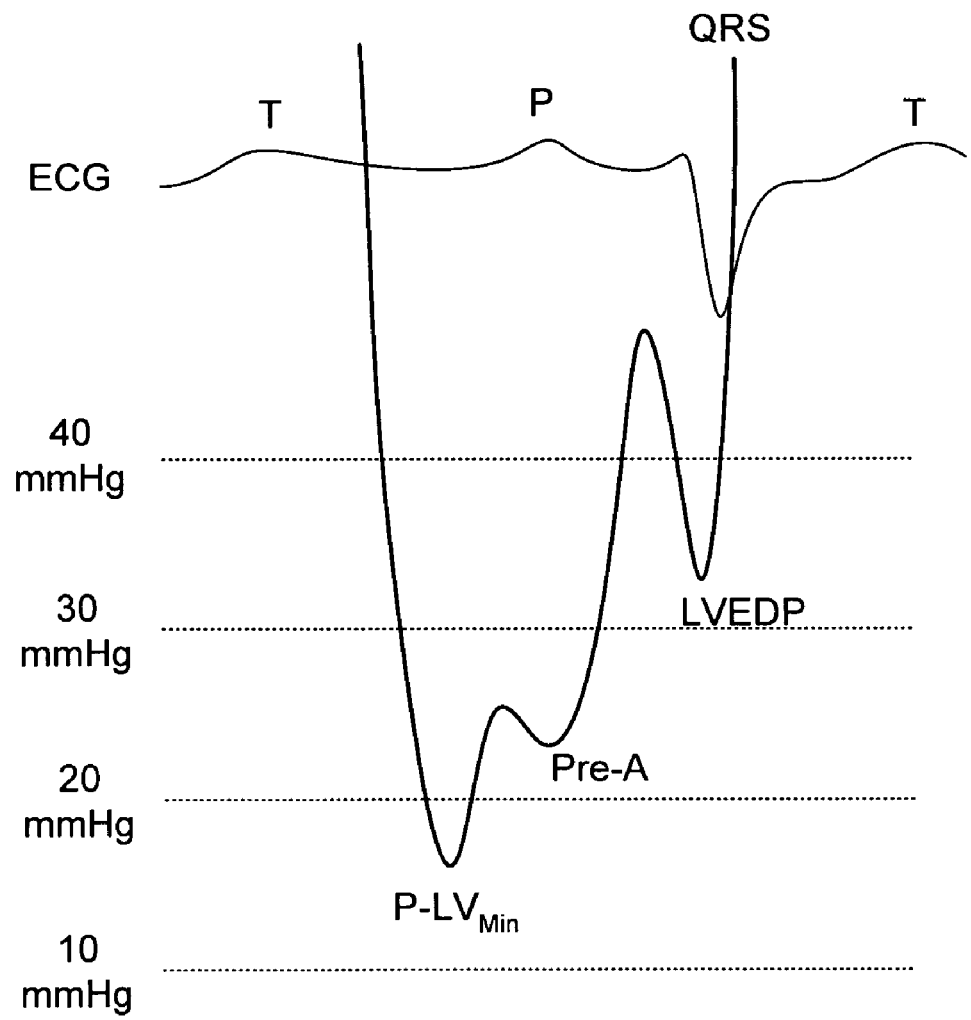
FIG. 6 is a plot of left ventricular filling pressure versus time and a corresponding ECG.

FIG. 6 shows a more detailed plot 600 of left ventricular filling pressures versus time. The left ventricular filling pressure falls to a minimum value ($P\text{-}LV_{Min}$) after the peak of the T-wave thereafter the pressure reaches a pre-atrial contraction value (Pre-A) and then reaches an end diastolic pressure value (LVEDP) just before a rise due to systole.

With respect to pulmonary edema, this condition is associated with a transfer of fluid from the pulmonary capillaries to the pulmonary interstitium and alveoli. Pulmonary edema of cardiac origin usually results from an increase in pulmonary capillary pressure caused by an elevation of left atrial pressure as often associated with left ventricular failure. Where left ventricular filling pressures cannot be measured directly, some surrogates exist. The measurement of pulmonary capillary wedge pressure (PCWP) provides an indirect measure of left atrial pressure and is particularly useful in the diagnosis of left ventricular failure. When the PCWP exceeds about 20 mmHg, the transmission of this pressure back into the pulmonary vasculature increases pulmonary capillary hydrostatic pressure which can lead to pulmonary congestion and edema.

Other measures may be used to assess pulmonary edema or related conditions. For example, transthoracic impedance can be used as a surrogate of lung fluidity. As already mentioned, mechanisms exist for left atrial pressure measurement as well. In general, a LVEDP of about 25 mmHg or more is indicative of pulmonary edema. PCWP typically underestimates LVEDP, for example, a PCWP of about 22 mmHg may correspond to a LVEDP of about 25 mmHg. Accordingly, where a surrogate pressure is used, a threshold pressure may be adjusted based on the surrogate.

A study by Drazner et al., "Relationship between right and left-sided filling pressures in 1000 patients with advanced heart failure," *J Heart Lung Transplant*, 1999 November; 18(11):1126-32, reported relationships between various pressures. For example, Drazner et al. reported that pulmonary artery systolic pressure (P-PAS) correlated very closely with pulmonary capillary wedge pressure (P-PCW), and could be estimated as two times the PCW pressure. Further, right atrial pressure correlated with PCW pressure: elevated right sided pressures (e.g., P-RA>10 mm Hg) were found to be reliable almost 80% of the time for the detection of elevated left-sided pressure (e.g., P-PCW>22 mmHg) in patients with a primary diagnosis of chronic heart failure. Thus, Drazner et al. concluded that "accurate estimation of RA pressure can potentially guide therapy of left ventricular filling pressures in approximately 80% of chronic heart failure patients without obvious non-cardiac disease" and that "in this population, elevated PAS pressures are largely determined by elevated left-sided filling pressures". Consequently, right atrial pressure (P-RA) or pulmonary artery systolic pressure (P-PAS) measurements may be used as indicators of congestion or an elevated filing pressure.

Another study by Chaliki et al., "Pulmonary venous pressure: Relationship to pulmonary artery, pulmonary wedge, and left atrial pressure in normal, lightly sedated dogs", *Cathet Cardiovasc Intervent*, 2002; 56:432-438, reported that mean pulmonary wedge pressure (mP-PCW) was virtually identical to mean left atrial pressure (mP-LA). Further, they reported that mean pulmonary venous pressure (mP-PV: 17.1±6.5 mm Hg) was intermediate between mean pulmonary artery pressure (mP-PA: 20.2±6.2 mm Hg) and mean pulmonary wedge pressure (mP-PCW: 13.3±6.2 mm Hg; or mean left atrial pressure (mP-LA: 13.4±6.3 mm Hg).

Yet another study by Yamamoto et al., "Assessment of mean left atrial pressure from the left ventricular pressure tracing in patients with cardiomyopathies," *Am J Cardiol*, 1996 Jul. 1; 78(1):107-10, reported that mean LV diastolic pressure provides a better assessment of mean left atrial pressure than LV pre-a-wave [P-wave] pressure or LV end-diastolic pressure. In turn, mean left atrial pressure (mP-LA) may provide an assessment of mean LV diastolic pressure (mP-LVD). In general, measurement of right side pressures, including pulmonary artery and pulmonary wedge, are more easily achieved than left side pressures. However, left side pressures, especially left atrial pressure, may be achieved through use of various lead-based sensors (see, e.g., aforementioned U.S. Patent Application US2003/0055345 A1, to Eigler et al.).

FIG. 7 shows an exemplary table 700 of pressures that may be used to assess filling pressure along with possible normal values and possible limit values that may distinguish wet from dry hemodynamic profiles. For example, a right atrial pressure (P-RA) in excess of approximately 10 mm Hg may indicate that filling pressure is elevated and hence congestion exists. Measurement of pressures may be achieved using any of a variety of pressure sensors.

Figure 8:
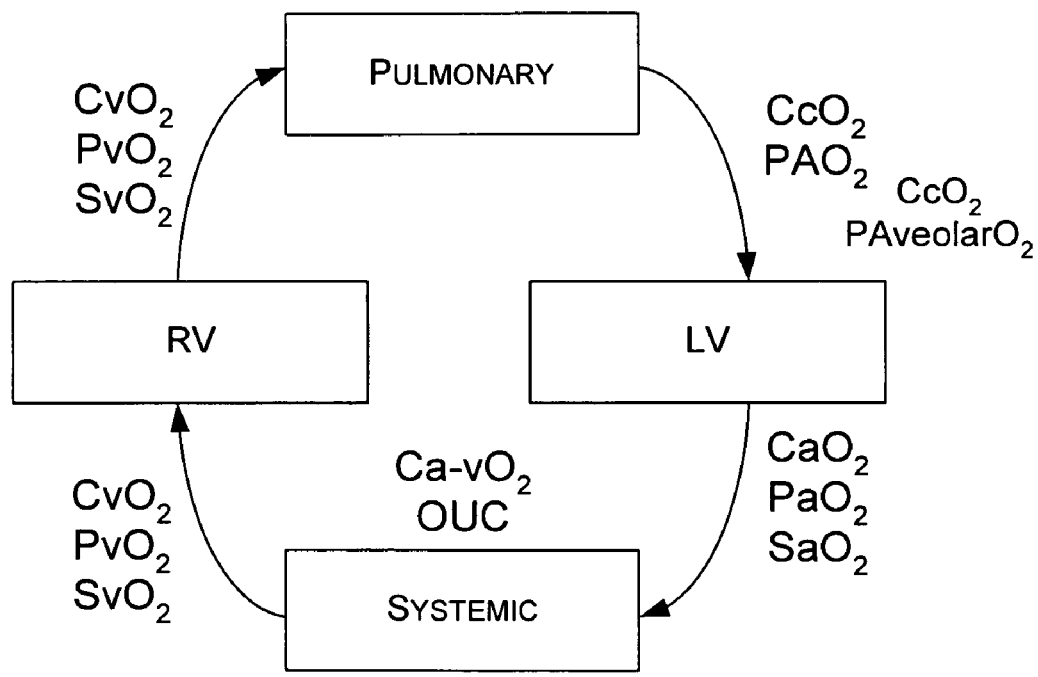
FIG. 8 is an exemplary schematic of various exemplary perfusion measures that may be used in determining a patient's hemodynamic profile.

Referring again to the perfusion parameter of FIGS. 3 and 4, various mechanisms exist for assessing perfusion. In general, hypoperfusion can be assessed by any of a variety of surrogates measures such as contractility, cardiac output, narrowing amplitude swing of blood pressure. Chemical measures such as differential of $SaO_2$ (arterial oxygen saturation) and $SvO_2$ (venous oxygen saturation) can be used as surrogates for perfusion. FIG. 8 shows various perfusion measures 800 with respect to the circulatory system. The right ventricle provides deoxygenated blood to the pulmonary system via the pulmonary artery (see, e.g., FIG. 1), the pulmonary system provides oxygenated blood to the left atrium via the pulmonary vein, the left atrium provides oxygenated blood to the left ventricle, the left ventricle provides oxygenated blood to the aorta and the body, and deoxygenated blood returns to the right ventricle via the inferior and superior vena cava. Exemplary parameters are shown, various of these parameters may be measurable or calculatable and indicators of perfusion.

Measurable parameters include arterial oxygen pressure ($PaO_2$), arterial carbon dioxide pressure ($PaCO_2$), arterial oxygen saturation ($SaO_2$ or $SpO_2$), mixed venous oxygen saturation ($SvO_2$), venous oxygen pressure ($PvO_2$), hemoglobin (Hgb), and cardiac output (CO) while calculatable parameters include pulmonary capillary oxygen content ($CcO_2$), arterial oxygen content ($CaO_2$), venous oxygen content ($CvO_2$), arterial-venous oxygen content difference ($Ca-vO_2$), oxygen utilization coefficient (OUC), oxygen delivery index ($DO_2I$), oxygen consumption index ($VO_2I$), intrapulmonary shunt (Qsp/Qt), and cardiac index (CI).

In conventional catheterization, a pulmonary artery catheter can provide a care provider with an ability to monitor oxygen transport balance through continuous mixed venous oximetry ($SvO_2$) as well as intermittent calculation of oxygen delivery ($DO_2I$) and oxygen consumption ($VO_2I$). As with the hemodynamic calculations, various oxygen transport parameters may be categorized as measurable or calculatable.

With respect to mixed venous oximetry, measurement of $SvO_2$ can indicate a relative balance between $VO_2I$ and $DO_2I$. Such information has been used to provide an early warning to detect onset of oxygen transport imbalance, to evaluate the efficacy of therapeutic interventions such that physiologic end-points are reached more quickly, to identify potentially detrimental consequences of "patient care" that might otherwise go unnoticed, etc.

In general, $SvO_2$ is a "flow-weighted average" of the venous saturations from all perfused vascular beds; thus, $SvO_2$ does not reflect the oxygen transport adequacy of non-perfused vascular beds nor does a "normal" $SvO_2$ mean that all tissues are adequately oxygenated. $SvO_2$ is an average estimate of venous saturation for the whole body and provides an assessment of the overall balance between $VO_2I$ and $DO_2I$, but does not yield information about the adequacy of perfusion of any individual vascular bed. If the $SvO_2$ falls, $VO_2I$ is increasing (and may lead to anaerobic metabolism if $DO_2I$ is not sufficient) or $DO_2I$ is decreasing. If the $SvO_2$ increases, $VO_2I$ is decreasing, $DO_2I$ is increasing, blood is possibly being shunted pass vascular beds without releasing its oxygen (such as in sepsis or cirrhosis), or oxygen uptake by the tissues may be decreased. Determinants of $SvO_2$ include Hgb, cardiac output (CO), $SaO_2$, and $VO_2I$ and the four main causes of low $SvO_2$ are anemia, low cardiac output, arterial desaturation, and increased $VO_2I$.

As described herein, various exemplary devices, methods, systems, etc., acquire information germane to a patient's hemodynamic profile via implantable sensors, external sensors or sensors that are both implantable and external. Implantable sensors include lead-based and other sensors capable of implantation and operation in vivo. External sensors include those that contact a patient's body and those that may not require body contact (e.g., infrared body temperature sensor, such as an IR camera, etc.).

Impedance may be measured using implantable sensor or external sensor technology. Impedance may indicate whether congestion or hypoperfusion exist. For example, a daily impedance trend may be used or used in conjunction with an absolute value. An exemplary device may calculate a difference between a one week average and a one month average. In this example, a negative difference (1 week average much lower than 1 month) may be used to indicate possible on-set of congestion. Such a measure may be used to indicate recovery or improving cardiac condition as well.

Figure 9:
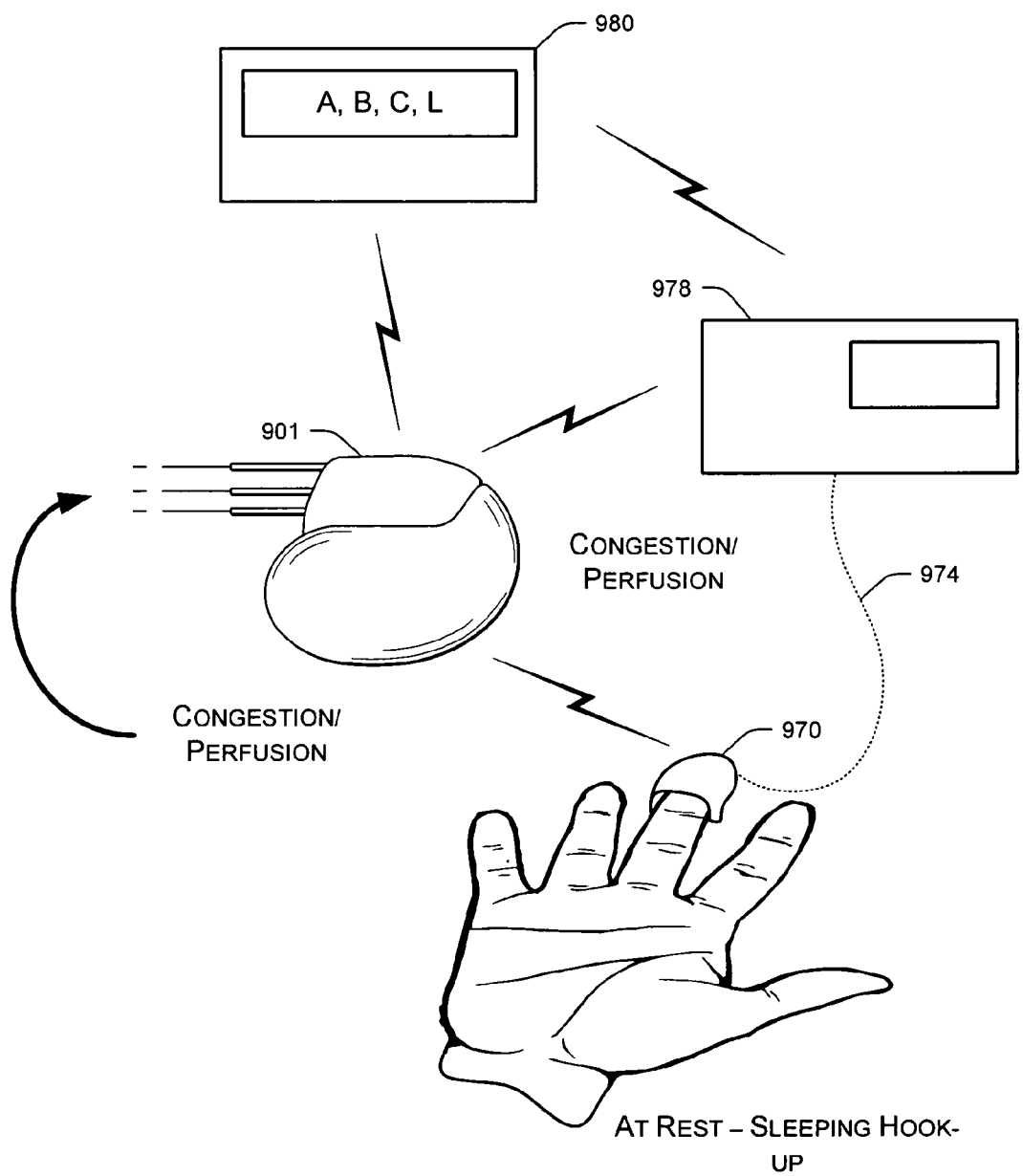
FIG. 9 is a diagram of various components of an exemplary system that includes an implantable device and optionally includes external sensors or units.

FIG. 9 shows an exemplary system 900 for monitoring a patient's hemodynamic profile. The exemplary system 900 includes an exemplary implantable device 901 and optionally one or more additional components. The implantable device 901 may acquire information germane to a patient's hemodynamic profile via one or more sensors connected to the device 901 or via one or more other sensors. For example, an external sensor 970 may acquire information germane to a patient's hemodynamic profile (e.g., evidence of congestion, evidence of hyoperfusion, etc.) and communicate such information to the implantable device 901 via a wireless mechanism. The external sensor 970 may rely on a link 974 between the sensor 970 and a unit 978 where the unit 978 communicates with the implantable device 901 or a programmer 980 for the implantable device 901. An implantable sensor may be used that communicates via a wireless mechanism or that otherwise relies on transmission of a signal through the body (e.g., body tissue, body fluid, etc.).

An exemplary system optionally relies on two or more temperature sensors. Such a system may provide a temperature differential, for example, between two spaced sensors, whereby the differential relates to perfusion (e.g., adequate to compromised).

An exemplary programmer (e.g., the programmer 980) may rely on information acquired by one or more implantable sensors in communication with the implantable device 901 (e.g., wired, wireless, etc.) or one or more external sensors (e.g., the external sensor 970) to determine a patient's hemodynamic profile (e.g., A, B, C or L, etc.). Of course, where appropriate, hybrid sensors that are part implantable and part external may be used. An exemplary implantable device (e.g., the implantable device 901) may rely on acquired information to similarly determine a patient's hemodynamic profile (e.g., A, B, C or L, etc.).

An exemplary implantable device optionally adjusts a therapy implementable by the implantable device based at least in part on information germane to a patient's hemodynamic profile. For example, an exemplary implantable device may determine a hemodynamic profile and then adjust a cardiac pacing therapy based on the hemodynamic profile. Referring to the scheme 400 of FIG. 4, such an exemplary implantable device may acquire information, determine a profile selected from a group of A, B, C and L profiles and then adjust a cardiac pacing therapy in response to the determined profile. An exemplary programmer may operate in a similar manner whereby the programmer acquires information, determines a profile selected from a group of A, B, C and L profiles and then determines an adjusted therapy capable of being administered, at least in part, by the implantable device. Such a programmer may further communicate therapy information to the implantable device for administration of the therapy (e.g., one or more pacing parameters, shock parameters, etc.).

Acquisition of Information by an exemplary implantable device or information otherwise relied up in determining a patient's hemodynamic profile is optionally dependent upon patient activity. For example, acquisition of such information may occur during a low activity state only where an activity sensor, clock, timer, etc. (see, e.g., the exemplary device 100 of FIG. 2 and corresponding description), aid in determining a patient's activity state. As described herein, various exemplary methods, devices, systems, etc., rely on a patient rest state prior to acquisition of information for use in determining a patient's hemodynamic profile. Various exemplary methods, devices, systems, etc., optionally filter or weigh information based on patient activity.

With respect to external sensors (or hybrid sensors), in various scenarios, use of such sensors may occur during patient rest (e.g., sleep). For example, prior to sleep a patient may attach an oximeter or temperature sensor to a finger. In this example, data acquisition unit may acquire oxygen or temperature information. During sleep or at a time thereafter, the information may be communicated to an exemplary implantable device. Further, in this example, a hemodynamic profile for the patient may be determined during sleep (or at a time thereafter) by the implantable device, the data acquisition unit. Yet further, therapy adjustment may occur based at least in part on the hemodynamic profile.

Figure 10:
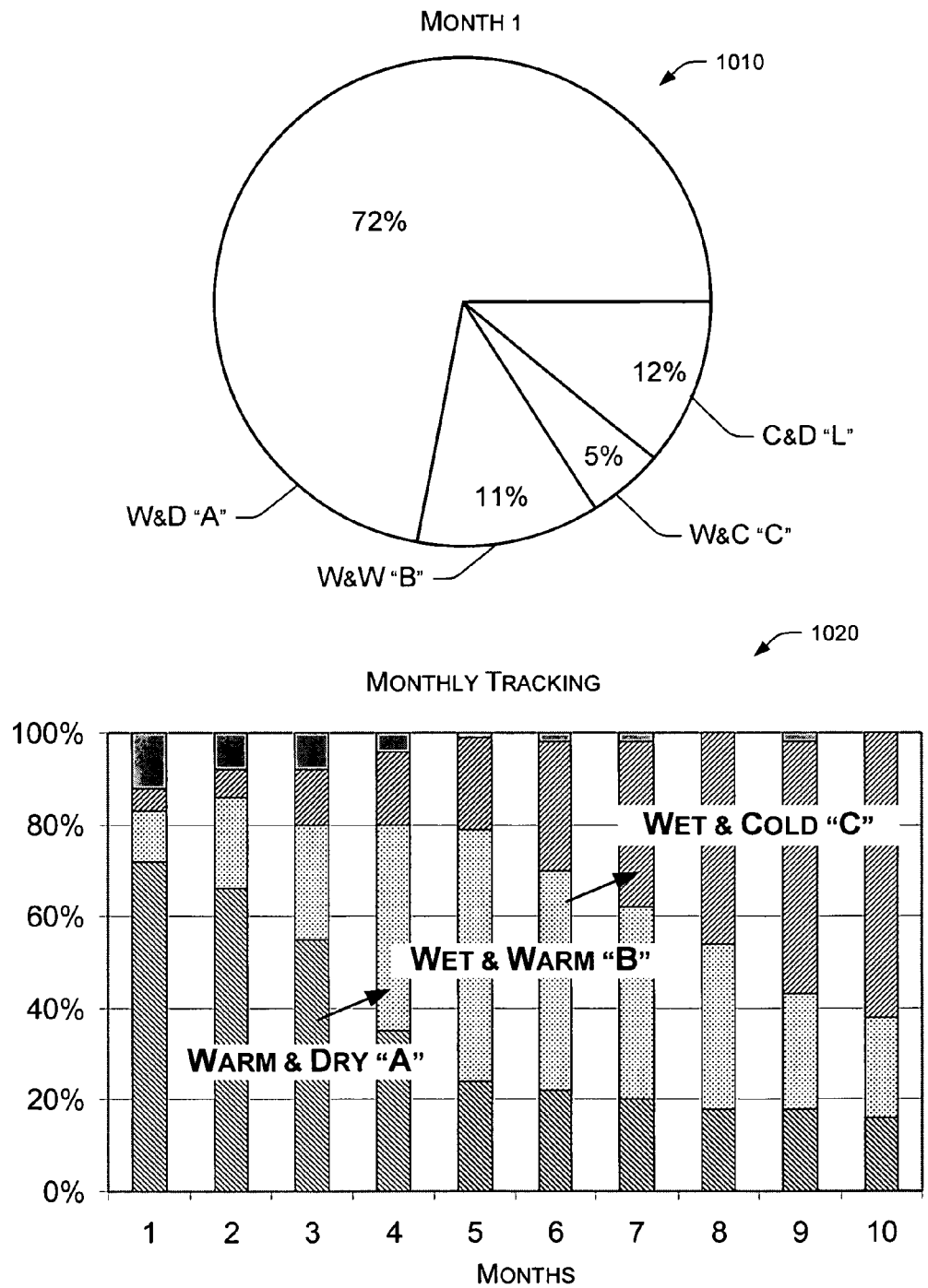
FIG. 10 is a series of exemplary plots of hemodynamic profile information.

FIG. 10 shows exemplary historic hemodynamic profiles 1000 that may be determined on the basis of information acquired at least in part by an exemplary implantable device (e.g., the device 100 of FIGS. 1 and 2, the device 901 of FIG. 9, etc.). The historic profile 1010 represents various hemodynamic profiles determined over a period of one month. The historic profile 1010 includes aforementioned A, B, C and L profiles where the patient experienced primarily profile A (72%) over the course of a month. While the profile 1010 relies on percentages, indexes other than percentages may be used. The information in the historic profile 1010 can aid a care provider in determining a course of therapy or be relied by an automatable process algorithm to determine a course of therapy.

Various exemplary implantable devices optionally acquire information germane to a patient's hemodynamic profile and then determine a hemodynamic profile that can be used to construct a hemodynamic profile history. For example, an exemplary implantable device may construct a profile such as the historic profile 1010.

A monthly tracking hemodynamic profile 1020, a form of historic profile as it includes historic information, shows a progression over a ten month period. During the first three months, the patient has profile A (Warm & Dry), a progression to profile B (Wet & Warm) occurred during months 4 to 7, and a progression to profile C (Wet & Cold) occurred during months 8 to 10. Such progressions may be used to monitor a patient or used at least in part to adjust or select a therapy for the patient.

Hemodynamic profile monitoring as described herein can serve as a CHF diagnostic classifier, as a surrogate CHF status trend, as a basis for medication therapy decisions, etc.

Figure 11:
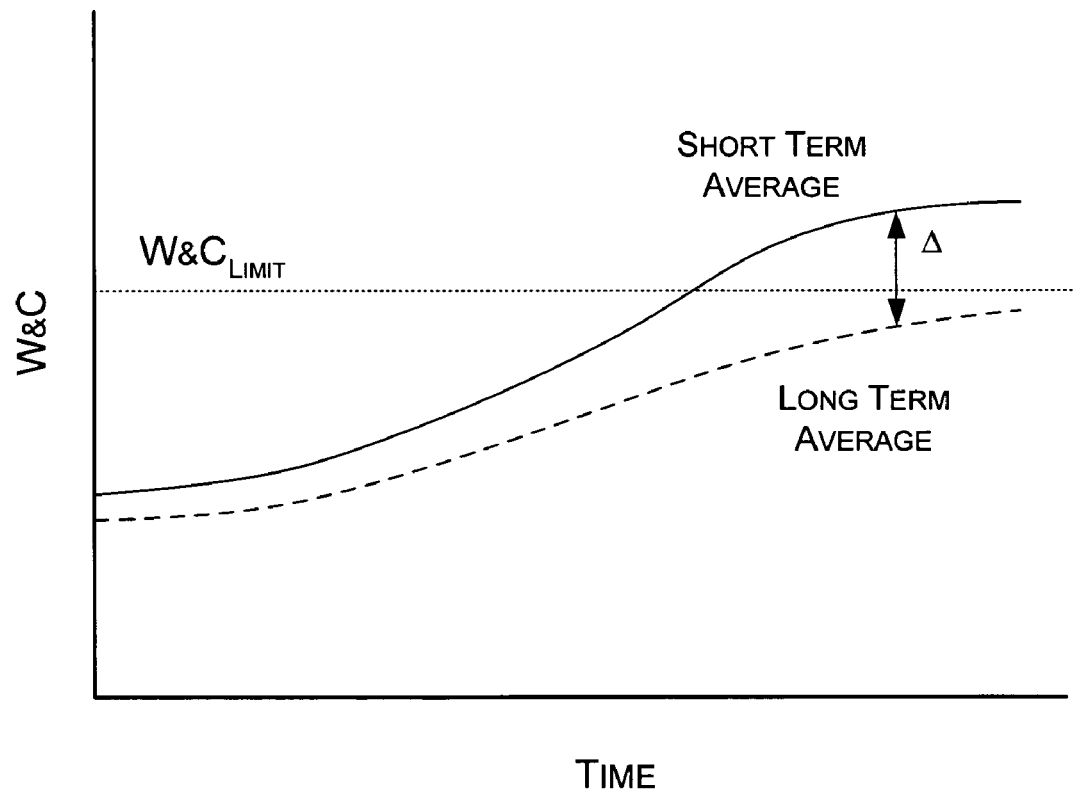
FIG. 11 is a plot illustrating an exemplary alarm mechanism for a Wet and Cold measure such as percentage of total time a patient is in a Wet and Cold condition.

FIG. 11 shows an exemplary plot 1100 of a W&C measure versus time. In this example, the W&C measure is percentage of total time a patient is in a W&C condition per a short term average (e.g., days, a week, etc.) and a long term average (e.g., one month, etc.). If a patient is in a stable condition, the short term and the long term average should coincide within some acceptable error. However, if the patient's condition worsens, then the short term average will reflect this change in condition more readily. Consequently, the short term average will differ from the long term average, which is illustrated by a value $\Delta$. This value may be compared to a threshold value (e.g., $\Delta_{Th}$) while the short term or long term value may be compared to a W&C percentage limit (e.g., $W\&C_{Limit}$). Such a comparison or comparisons may be used to trigger an alarm or to adjust therapy.

Figure 12:
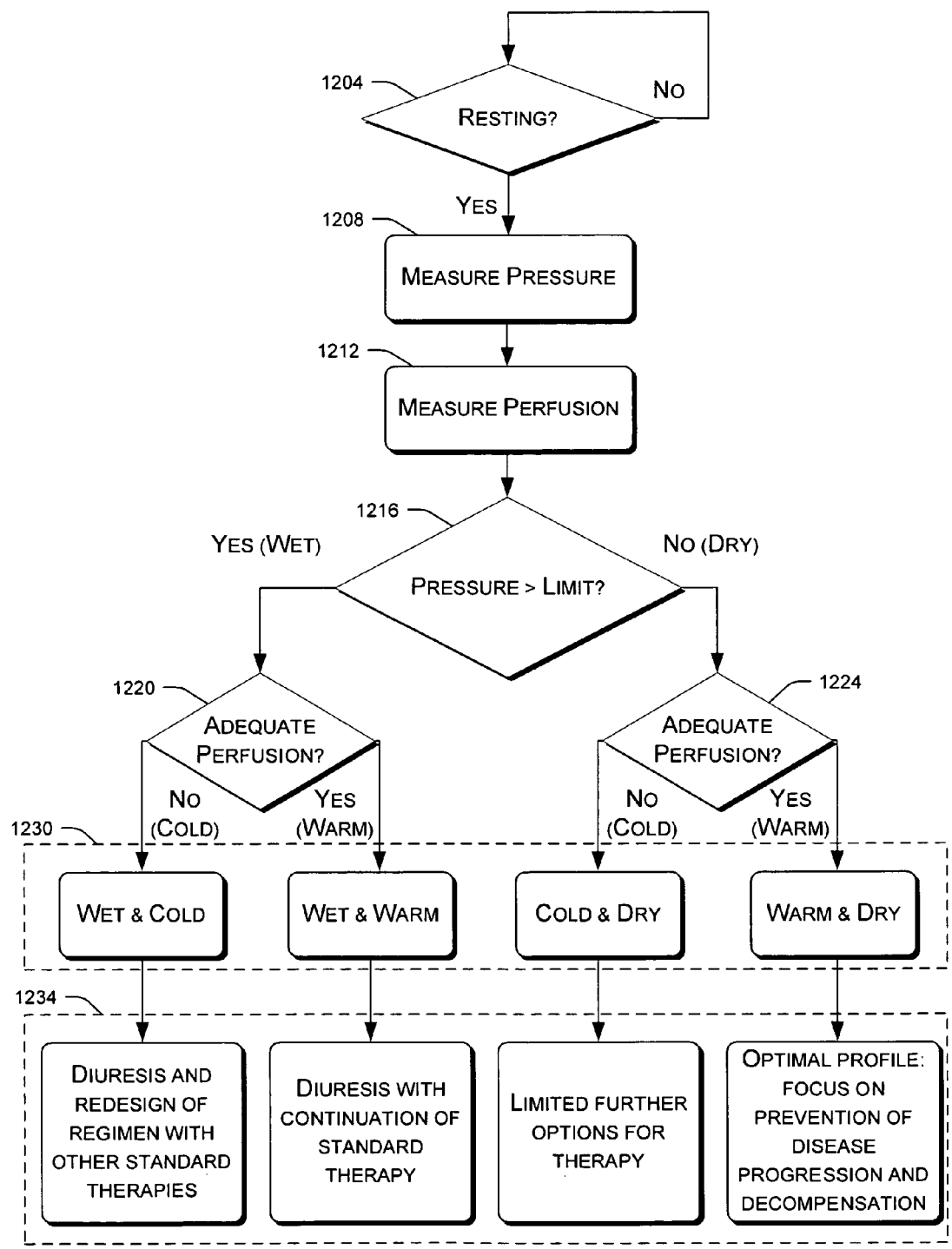
FIG. 12 is a block diagram of an exemplary method for acquiring information germane to a patient's hemodynamic profile and determining a patient's hemodynamic profile.

FIG. 12 shows an exemplary method 1200 for monitoring a patient's hemodynamic profile and optionally adjusting the patient's therapy based at least in part on hemodynamic profile. The method 1200 commences in an activity monitoring block 1204 that decides if the patient is resting. If the patient is not resting then activity monitoring continues. As already mentioned, activity information may be associated with other acquired information and then used to filter or otherwise compensate for activity state. If the activity monitoring decision block 1204 decides that the activity is indicative of a resting state, then the method continues in one or more measurement blocks such as a pressure measurement block 1208 and a perfusion measurement block 1212. The measured pressure and the measured perfusion may be used directly as a pressure parameter and a perfusion parameter, respectively, or be used to determine an appropriate pressure parameter or an appropriate perfusion parameter.

Once information regarding filling pressure and perfusion has been acquired, the exemplary method 1200 enters a hemodynamic profiling process. In this example, a decision block 1216 decides if the measured pressure or other pressure parameter exceeds a limit. If the decision block 1216 decides that the pressure exceeds the limit, then the profile is deemed "wet" otherwise the profile is deemed "dry". Both branches of the decision block 1216 lead to respective decision blocks for perfusion 1220, 1224 where measured perfusion or a perfusion parameter is used to make a decision as to whether the profile is "cold" or "warm". The decision blocks 1220, 1224 lead to a profiling block 1230 where one of four profiles is determined based on the pressure parameter and the perfusion parameter.

According to the exemplary method 1200, the profiling block 1230 leads to a therapy block 1234 that associates the profile with a therapy (see, e.g., the scheme 400 of FIG. 4 and related description).

Where an exemplary implantable device implements the exemplary method 1200, the therapy block 1234 may specify operational parameters for the implantable device. For example, with respect to diuresis, such parameters may be related to pacing therapies that can have some effect on diuresis. One study, Zullo, "Characteristics of the acute rise of atrial natriuretic factor during ventricular pacing", *Chest* (2002); 121: 1942-1946, noted a urinary response to ventricular pacing (e.g., known that levels of atrial natriuretic factor (ANF) are elevated during ventricular (VVI) pacing and that this peptide has natriuretic, diuretic, and vasodilator properties). Zullo noted that several patients exhibited a significant diuresis during VVI pacing, that the entire study group appeared to show an increase in urinary flow rates and that a known decrease in cardiac output during VVI pacing exists. Consequently, a relationship may exist between urinary flow and various pacing therapies whereby the therapy block 1234 may act to implement such therapies.

Where a therapy includes cardiac pacing, such pacing may rely on stimulation of a single ventricle or both ventricles with or without atrial pacing (e.g., to one or both atria). With respect to biventricular pacing, parameters typically include an interventricular delay (VV) and one or more atrio-ventricular delays (e.g., PV, $PV_{RV}$, $PV_{LV}$, AV, $AV_{RV}$, $AV_{LV}$). Cardiac therapy delivered by an implantable cardiac therapy device optionally includes activation (e.g., stimulation, etc.) of tissue other than the myocardium. For example, autonomic activation may occur through delivery of energy to a sympathetic nerve, a parasympathetic nerve or a nerve bundle having both sympathetic and parasympathetic nerves.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   providing a filling pressure parameter;
   providing a perfusion parameter;
   determining a hemodynamic profile based at least in part on the filling pressure parameter and the perfusion parameter, wherein the hemodynamic profile comprises a profile selected from a group consisting of warm and dry, wet and warm, wet and cold, and cold and dry; and
   adjusting a stimulation parameter of an implantable cardiac therapy device based at least in part on the hemodynamic profile.

2. The method of claim 1 further comprising providing at least one of the filling pressure parameter and the perfusion parameter to the implantable cardiac therapy device via a wireless link.

3. The method of claim 1 wherein the providing the filling pressure parameter comprises measuring an intravenous pressure.

4. The method of claim 1 wherein the providing the filling pressure parameter comprises measuring a cardiac chamber pressure.

5. The method of claim 1 wherein the providing the perfusion parameter comprises measuring a temperature.

6. The method of claim 1 wherein the providing the perfusion parameter comprises using oximetry.

7. The method of claim 1 wherein the providing the perfusion parameter comprises measuring an impedance.

8. The method of claim 1 wherein the providing the filling pressure parameter comprises measuring impedance.

9. The method of claim 1 wherein the stimulation parameter comprises a biventricular pacing therapy parameter.

10. A method comprising:
    providing a filling pressure parameter wherein the filling pressure parameter indicates whether the hemodynamic profile is wet or dry;
    providing a perfusion parameter;
    determining a hemodynamic profile based at least in part on the filling pressure parameter and the perfusion parameter; and
    adjusting a stimulation parameter of an implantable cardiac therapy device based at least in part on the hemodynamic profile.

11. A method comprising:
    providing a filling pressure parameter;
    providing a perfusion parameter wherein the perfusion parameter indicates whether the hemodynamic profile is cold or warm;
    determining a hemodynamic profile based at least in part on the filling pressure parameter and the perfusion parameter; and
    adjusting a stimulation parameter of an implantable cardiac therapy device based at least in part on the hemodynamic profile.

12. A method comprising:
    providing a filling pressure parameter;
    providing a perfusion parameter;
    determining a hemodynamic profile based at least in part on the filling pressure parameter and the perfusion parameter; and adjusting a stimulation parameter of an implantable cardiac therapy device based at least in part on the hemodynamic profile; and further comprising determining an activity state and performing the determining only during a predetermined activity state.

13. A system comprising:

means for providing a filling pressure parameter wherein the filling pressure parameter indicates whether the hemodynamic profile is wet or dry;

means for providing a perfusion parameter;

means for determining a hemodynamic profile based at least in part on the filling pressure parameter and the perfusion parameter; and means for adjusting a stimulation parameter of an implantable cardiac therapy device based at least in part on the hemodynamic profile.

* * * * *